US008895047B2

(12) United States Patent
Gupta et al.

(10) Patent No.: US 8,895,047 B2
(45) Date of Patent: *Nov. 25, 2014

(54) COMBINED FIBRINOLYTIC AND ANTIMICROBIAL CATHETER AND USES THEREOF

(75) Inventors: Nisha Gupta, Audubon, PA (US); Joel Rosenblatt, Pottstown, PA (US); Daniel J. Spangler, Fort Worth, TX (US)

(73) Assignee: Arrow International, Inc., Reading, PA (US)

(*) Notice: Subject to any disclaimer, the term of this patent is extended or adjusted under 35 U.S.C. 154(b) by 700 days.

This patent is subject to a terminal disclaimer.

(21) Appl. No.: 12/451,773

(22) PCT Filed: May 21, 2008

(86) PCT No.: PCT/US2008/006492
§ 371 (c)(1),
(2), (4) Date: Mar. 1, 2010

(87) PCT Pub. No.: WO2008/150375
PCT Pub. Date: Dec. 11, 2008

(65) Prior Publication Data
US 2010/0196434 A1    Aug. 5, 2010

Related U.S. Application Data

(60) Provisional application No. 60/932,759, filed on Jun. 1, 2007.

(51) Int. Cl.
```
A61F 2/00      (2006.01)
A61K 38/49     (2006.01)
A61K 31/155    (2006.01)
A61K 31/135    (2006.01)
A61K 31/65     (2006.01)
A61K 31/497    (2006.01)
A61L 33/00     (2006.01)
A61L 29/16     (2006.01)
A61K 38/48     (2006.01)
A61M 25/00     (2006.01)
```

(52) U.S. Cl.
CPC ........ *A61L 29/16* (2013.01); *A61M 2025/0056* (2013.01); *A61L 2300/42* (2013.01); *A61L 2300/404* (2013.01); *A61L 2300/206* (2013.01); *A61L 2300/406* (2013.01); *A61L 2300/442* (2013.01); *A61L 33/0047* (2013.01); *A61L 2300/45* (2013.01)
USPC ............. 424/423; 424/94.63; 424/94.64; 514/635; 514/648; 514/152; 514/254.11

(58) Field of Classification Search
CPC .......... A61L 2300/404; A61L 2300/42; A61L 2300/45; A61L 2300/442; A61L 2300/406; A61L 2300/206; A61L 33/0047; A61M 2025/0056; C12Y 304/21073; A61K 38/49; C07C 279/26
USPC ............. 424/423, 94.64, 94.63; 514/254.11, 514/648, 152, 635
See application file for complete search history.

(56) References Cited

U.S. PATENT DOCUMENTS

| | | | | |
|---|---|---|---|---|
| 6,416,546 B1 * | 7/2002 | Kimura et al. | ............... | 623/1.46 |
| 2001/0003599 A1 * | 6/2001 | Chinn et al. | ................. | 427/2.24 |

(Continued)

FOREIGN PATENT DOCUMENTS

| | | |
|---|---|---|
| JP | 10211272 A | 8/1998 |
| JP | 10-328293 | 12/1998 |

(Continued)

OTHER PUBLICATIONS

Molecular Innovations, Urokinase (uPA) International Units [Retrieved from internet <URL: http://www.mol-innov.com/knowledgebase/urokinase-upa-international-units/ >], [Downloaded Jul. 7, 2014], 2 pages.*

(Continued)

*Primary Examiner* — Jason Sims
*Assistant Examiner* — Miriam A Levin
(74) *Attorney, Agent, or Firm* — Baker & Hostetler LLP

(57) ABSTRACT

Implantable catheters are provided which comprise an antimicrobial agent incorporated in a coating or bulk distributed, in combination with a fibrinolytic agent incorporated in a top coating.

16 Claims, 7 Drawing Sheets

The Effect of CHA on uPA Activity

(56) References Cited

U.S. PATENT DOCUMENTS

2003/0028243 A1 2/2003 Bates et al.
2006/0025726 A1* 2/2006 Fischer et al. ............... 604/265
2007/0104758 A1 5/2007 Hamilton et al.

FOREIGN PATENT DOCUMENTS

| JP | 2005-334216 | 12/2005 |
| JP | 2005334216 A | 12/2005 |
| WO | 2005020905 A2 | 3/2005 |

OTHER PUBLICATIONS

PCT Notification of Transmittal of the International Search Report and The Written Opinion of the International Searching Authority, or The Declaration, dated Aug. 26, 2008 in connection with PCT International Patent Application No. PCT/US2008/006492, 9 pages.
Supplementary European Search Report for EP 08754605; dated Jun. 29, 2011.

* cited by examiner

US 8,895,047 B2

COMBINED FIBRINOLYTIC AND ANTIMICROBIAL CATHETER AND USES THEREOF

CROSS-REFERENCE TO RELATED APPLICATIONS

This application is a national stage entry under 35 U.S.C. §371 of PCT International Patent Application No. PCT/US2008/006492, filed May 21, 2008, and claims priority to U.S. Provisional Patent Application No. 60/932,759, filed Jun. 1, 2007, the contents of which are incorporated herein by reference in their entirety into the subject application.

FIELD OF THE INVENTION

The present invention relates to implantable catheters, such as central venous catheters, with an antimicrobial agent incorporated in the device either as a coating or bulk distributed, in combination with a fibrinolytic agent incorporated in a top coating, thereby preventing device-related infection and thrombosis.

BACKGROUND OF THE INVENTION

Various publications are referred to throughout this application. Full citations for these references may be found at the end of the specification immediately preceding the claims. The disclosures of these publications are hereby incorporated by reference in their entireties into the subject application to more fully describe the art to which the subject application pertains.

Implantable medical devices such as tunneled catheters play a major role in general medicine. Aside from pneumothorax and hemorrhage-like complications which are associated with their initial insertion, catheters are associated with the long-term risks of infection and thrombosis [e.g., Harter et al. 2002; Safdar and Maki 2003; Saint et al. 2000]. Colonization of microorganisms on the surfaces of such devices following implantation can produce serious and costly complications, including the need to remove and/or replace the implanted device and/or vigorous treatment of secondary infections. Within days of insertion, almost all central venous catheters (CVCs) are coated with a fibrin sheath, and within 30 days, most catheter-related thrombi arise. Aside from reducing the function of the catheter, these catheter-related thrombi can cause postphlebitic syndrome in 15%-30% cases and pulmonary embolism in 11% of the cases [Kuter 2004]. An association of CVC-related infection with CVC-related thrombosis has been suggested [Raad et al. 1994; Rooden et al. 2005]. To minimize the risk of infection, chlorhexidine-silver sulfadiazine-impregnated or minocycline-rifampin-impregnated catheters [Mermel 2000] and, to minimize thrombosis, anticoagulant-coated catheters are utilized in clinics [Carrasco et al. 2004; Long and Coulthard 2006].

The art describes treatment of medical devices with antimicrobial and anticoagulants alone or in combination to provide dual benefits [Hanna et al. 2006; U.S. Pat. Nos. 5,451, 424, 5,688,516, 5,707,366, 6,261,271, 6,273,875 B1, 6,528, 107 B2]. Attachment of fibrinolytic enzymes to provide an antithrombogenic surface for medical device applications is also described [U.S. Pat. Nos. 4,273,873, 4,378,435]. Bacteriostatic organic alcohols have been proposed as preservatives for use with catheters coated with tissue-plasminogen activator [U.S. 2006/0257390]. However, enzymes, such as fibrinolytics, can be inactivated by a number of agents, including antimicrobial agents [e.g., U.S. Pat. No. 4,483,922] such as chlorhexidine [Pellat et al. 1991]. Ethanol, for example, is known to inhibit activity induced by urokinase and streptokinase [Roszkowska-Jakimiec et al. 1988-1989]. Treatment with fibrinolytic agents in combination with antimicrobial agents and the compatibility of these two classes of agents, where one agent does not adversely affect the activity of the other, has not been defined despite the need for catheters having combined fibrinolytic and antimicrobial properties.

SUMMARY OF THE INVENTION

The present invention is based on the discovery of the compatibility of fibrinolytic enzymes such as urokinase, streptokinase and tissue type plasminogen activator (tPA), with antiseptics such as chlorhexidine (CHX) and/or gentian violet (GV), and antibiotics such as minocycline and/or rifampin. The invention provides implantable catheters comprising an antimicrobial agent, such as an antiseptic or antibiotic, incorporated in a coating or bulk distributed, in combination with a fibrinolytic agent incorporated in a top coating, wherein the presence of the antimicrobial agent does not decrease the fibrinolytic activity of the fibrinolytic agent or wherein the presence of the fibrinolytic agent does not decrease the antimicrobial activity of the antimicrobial agent.

DETAILED DESCRIPTION OF THE INVENTION

Figure 1:
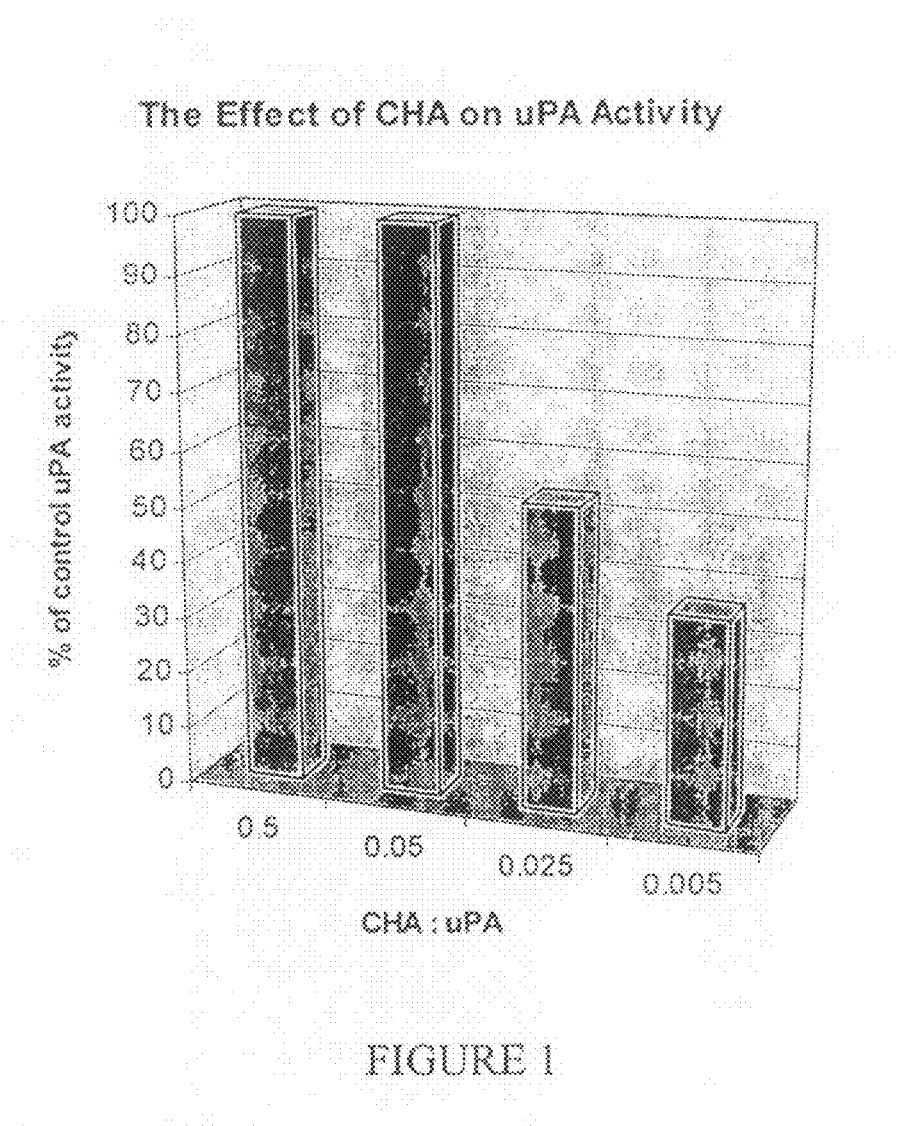
FIG. 1. Urokinase (uPA) activity in the presence of chlorhexidine acetate (CHA) at different concentrations. The plot shows percent of uPA control activity against the ratio of CHA to uPA (w/w); uPA Control=uPA activity in absence of CHA.

The invention provides an implantable catheter comprising an antimicrobial agent incorporated in a coating or bulk distributed, in combination with a fibrinolytic agent incorporated in a top coating, wherein the antimicrobial agent does not decrease the fibrinolytic activity of the fibrinolytic agent or wherein the fibrinolytic agent does not decrease the antimicrobial activity of the antimicrobial agent.

As used herein, "wherein the antimicrobial agent does not decrease the fibrinolytic activity of the fibrinolytic agent" means that the antimicrobial agent does not reduce the activity of the fibrinolytic agent by more than 50%. Preferably, the antimicrobial agent does not reduce the activity of the fibrinolytic agent by more than 25%, more preferably by not more than 10%, and most preferably the antimicrobial agent does not interfere with the activity of the fibrinolytic agent. Said in another way, the activity of the fibrinolytic agent in the combination is not reduced by more than 50%, preferably not more than 25%, more preferably not more than 10%, and most preferably not at all, relative to the activity of the fibrinolytic agent in the absence of the antimicrobial agent.

As used herein, "wherein the fibrinolytic agent does not decrease the antimicrobial activity of the antimicrobial agent" means that the fibrinolytic agent does not reduce the activity of the antimicrobial agent by more than 50%. Preferably, the fibrinolytic agent does not reduce the activity of the antimicrobial agent by more than 25%, more preferably by not more than 10%, and most preferably the fibrinolytic agent does not interfere with the activity of the antimicrobial agent. Said in another way, the activity of the antimicrobial agent in the combination is not reduced by more than 50%, preferably not more than 25%, more preferably not more than 10%, and most preferably not at all, relative to the activity of the antimicrobial agent in the absence of the fibrinolytic agent.

Preferably, the antimicrobial agent does not decrease the fibrinolytic activity of the fibrinolytic agent and the fibrinolytic agent does not decrease the antimicrobial activity of the antimicrobial agent, meaning, as used herein, that neither the fibrinolytic agent nor the antimicrobial agent reduces the activity of the other agent by more than 50%. Preferably, neither agent reduces the activity of the other agent by more than 25%, more preferably by not more than 10%, and most preferably neither agent interferes with the activity of the other agent. Said in another way, the activity of the fibrinolytic agent in the combination is not reduced by more than 50%, preferably not more than 25%, more preferably not more than 10%, and most preferably not at all, relative to the activity of the fibrinolytic agent in the absence of the antimicrobial agent; and the activity of the antimicrobial agent in the combination is not reduced by more than 50%, preferably not more than 25%, more preferably not more than 10%, and most preferably not at all, relative to the activity of the antimicrobial agent in the absence of the fibrinolytic agent.

In accordance with the present invention, tests for determining the compatibility of fibrinolytic and antimicrobial agents and whether the presence of one agent decreases the activity of the other agent are carried out as set forth in the Experimental Details presented herein below.

Agents can be coated on the catheter and/or incorporated in the catheter material during manufacture. Catheters can include a main body having a proximal portion, a distal portion and a lumen extending between the proximal portion and the distal portion of the main body. In some examples, the antimicrobial agent and the fibrinolytic agent can be disposed at different portions of the catheter, where the different portions may or may not overlap. At least a portion of the catheter can be impregnated with the antimicrobial agent. At least a portion of the catheter can be coated with the antimicrobial agent. For example, the antimicrobial agent can be disposed at least on the proximal portion of the main body and the fibrinolytic agent can be disposed at least on the distal portion of the main body. The agents can be disposed on the catheter in such a way that when the catheter is implanted in a subject, a desired agent is brought in contact with a desired region of the subject, for example a blood vessel, a body cavity, or subcutaneous space.

The fibrinolytic agent can be any agent that by direct or indirect action disperses, disrupts or dissolves fibrin-containing clots or proteinaceous aggregates. This can include indirect activation of plasminogen and/or direct effect on fibrin. Examples of fibrinolytic agents include urokinase, tissue-type plasminogen activator (tPA), streptokinase, nattokinase (soy), lumbrokinase (earthworm), serrapeptase (bacterial), desmoteplase (vampire bat), fibrolase and alfimeprase (snake). Fibrinolytic agents can also include fibrinolytically active fragments of full length fibrinolytic enzymes. Fibrinolytic agents also include synthetic chemical derivatives of fibrinolytic enzymes or their fragments such as polymer conjugates, PEGylated (polyethylene glycol) or carbohydrate conjugated versions. Fibrinolytic polymers can contain one or more fibrinolytic site(s) as conjugated side or pendant chains to the polymer backbone as well as having the fibrinolytic incorporated in the polymer backbone. Preferred fibrinolytic agents are urokinase, tissue-type plasminogen activator and streptokinase, with urokinase being the most preferred. The fibrinolytic agent can, for example, be crosslinked/immobilized to the polymeric surface of the catheter using either a crosslinking agent or a reactive polymer (such as a polyanhydride) or using a binding peptide or antibody that has an affinity for both the polymer surface as well as the fibrinolytic enzyme.

Antimicrobial agents include, for example, biguanides (including chlorhexidine, alexidine, PHMB—polyhexamethylbiguanide), antifungals (including gentian violet, azole and azole derivatives, rapamycin), phenolic antiseptics (e.g., triclosan, thymol), disulfuram, antimicrobial dyes (including gentian violet, methyl violet, methylene blue), cationic steroids, antimicrobial metal ions salts or conjugates (e.g., silver, silver sulfadiazine, zinc, copper, bismuth, gallium), biofilm inhibitors (including bismuth thiols, RIP [RNA III inhibiting peptide], furanones and their conjugates or derivatives, inhibitors of autoinducer 2, its kinases or its receptors, inhibitors of homoserine lactones, its kinases or its receptors), antibiotics and combinations (including tetracyclines, clindamycin, rifamycins, aminoglycosides, penicillins, cephalosporins, quinolones and fluoroquinolones, macrolides, carbapenems, glycopeptides (e.g., vancomycin, teicoplanin), polypeptides (e.g., bacitracin, polymixin B), sulfonamides, muciprocin, linezolid, chloramphenicol), oxidative antimicrobial agents (nitric oxide donors, N-chlorotaurine, organic and inorganic peroxides), chemotherapeutic agents (including DNA alkylating agents, mitomycin C, adriamycin, bleomycin, 5 fluorouracil, taurolidine, cisplatins, carboplatins), antimicrobial host defense proteins, host defense protein mimetics, their fragments and conjugates and salts thereof. The antimicrobial agent as used in the present invention includes organic alcohols such as, for example, ethanol, isopropanol and benzyl alcohol, in amounts that are bacteriocidal (and not merely preservatively effective amounts). Preferred antimicrobial agents are chlorhexidine, gentian violet, admixtures thereof, minocycline, rifampin, minocycline-rifampin, and salts thereof.

For example, the chlorhexidine in the catheter can be in the form of chlorhexidine base and/or a chlorhexidine salt that is compatible with the fibrinolytic agent. Chlorhexidine salts include, for example, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynaphthoate, chlorhexidine dilaurate, chlodhexidine dimyristate, chlorhexidine dipalmitate, chlorhexidine distearate and chlorhexidine embonate. Chlorhexidine acetate is a preferred form of chlorhexidine.

Preferably, the fibrinolytic agent and the antimicrobial agent are the following combinations: (1) the fibrinolytic agent is urokinase and the antimicrobial agent is chlorhexidine or a salt thereof; (2) the fibrinolytic agent is urokinase and the antimicrobial agent is gentian violet or a salt thereof; (3) the fibrinolytic agent is urokinase and the antimicrobial agent is an admixture of chlorhexidine and gentian violet or a salt thereof; (4) the fibrinolytic agent is urokinase and the antimicrobial agent is minocycline; (5) the fibrinolytic agent is urokinase and the antimicrobial agent is rifampin; (6) the fibrinolytic agent is urokinase and the antimicrobial agent is minocycline-rifampin; (7) the fibrinolytic agent is tissue-type plasminogen activator and the antimicrobial agent is chlorhexidine or a salt thereof; (8) the fibrinolytic agent is tissue-type plasminogen activator and the antimicrobial agent is gentian violet or a salt thereof; (9) the fibrinolytic agent is tissue-type plasminogen activator and the antimicrobial agent is an admixture of chlorhexidine and gentian violet or a salt thereof; (10) the fibrinolytic agent is tissue-type plasminogen activator and the antimicrobial agent is minocycline; (11) the fibrinolytic agent is tissue-type plasminogen activator and the antimicrobial agent is rifampin; (12) the fibrinolytic agent is tissue-type plasminogen activator and the antimicrobial agent is minocycline-rifampin; (13) the fibrinolytic agent is streptokinase and the antimicrobial agent is chlorhexidine or a salt thereof; (14) the fibrinolytic agent is streptokinase and the antimicrobial agent is gentian violet or a salt thereof; (15) the fibrinolytic agent is streptokinase and the antimicrobial agent is an admixture of chlorhexidine and gentian violet or a salt thereof; (16) the fibrinolytic agent is streptokinase and the antimicrobial agent is minocycline; (17) the fibrinolytic agent is streptokinase and the antimicrobial agent is rifampin; or (18) the fibrinolytic agent is streptokinase and the antimicrobial agent is minocycline-rifampin. Most preferred combinations are urokinase and one or more of chlorhexidine, gentian violet, minocycline, rifampin, minocycline-rifampin, or salts thereof.

The antimicrobial agent can be present in the catheter an amount effective to permit absorption of the antimicrobial agent from the catheter. The antimicrobial agent can be present in the catheter in a concentration of 0.01%-20% by weight of the catheter and preferably 0.1%-10% by weight of the catheter. In some examples, the range can be 0.5%-5% by weight of the catheter. The antimicrobial agent can have a concentration, for example, of about 200 micrograms per cm length of catheter.

The fibrinolytic agent can be present in the catheter in an amount effective to permit absorption of the fibrinolytic agent from the catheter. The fibrinolytic agent can be present from 1 U-1000 U (approx. 6-6000 ng) per cm length of catheter and preferably from 5 U-500 U per cm length of catheter.

Previously incompatible combinations of antimicrobial agents and fibrinolytic agents may be converted to compatible combinations by including fibrinolytic stabilizing surfactants, buffers, cyclodextrins, humectants or hydrophilic or amphiphilic polymers in the catheter or its coating layers. Also, in addition to separating potentially incompatible combinations (thereby compatibilizing them) by applying them to different regions of the catheter (e.g., proximal application—distal application), they can also be compatiblized by being kept separate by laminating an agent-free polymer separation layer between the fibrinolytic top coat and the antimicrobial containing layers beneath or by encapsulating the antimicrobial agent such that it does not directly interact with the fibrinolytic until it is released by diffusion from the catheter.

The catheter can be for implantation, for example, in a vessel such as a blood vessel or in a body cavity in a subject. Examples of such catheters include transcutaneous catheters; vascular catheters including peripheral catheters, central catheters, venous catheters, and arterial catheters; urinary catheters; and dialysis catheters.

The present invention is illustrated in the following Experimental Details section, which is set forth to aid in the understanding of the invention, and should not be construed to limit in any may the scope of the invention as defined in the claims that follow thereafter.

EXPERIMENTAL DETAILS

Compatibility of Urokinase with Antiseptic and Antibiotic Agents

To check the compatibility of urokinase (uPA) and chlorhexidine acetate (CHA), human urokinase enzyme (American Diagnostica) at different concentrations (0, 0.05, 0.5, and 1.0 µg/mL) was incubated with CHA at concentrations between 0-10 µg/mL for 24 hours at 37° C. in phosphate buffered saline (PBS). Subsequently, urokinase activity was measured using uPA Activity Assay Kit (Chemicon). Samples were incubated with an assay buffer and a chromogenic substrate for uPA resulting in the formation of a colored complex followed by reading the absorbance on a spectrophotometer at 405 nm.

Urokinase activity was not affected by the presence of CHA in the test solution if the CHA:uPA ratio was 0.05 or higher as shown in FIG. 1.

In a 96 well plate, different combinations of chlorhexidine (CHX), gentian violet (GV), minocycline and rifampin were incubated at concentrations of 0, 1, 10 µg/mL, for 24 hours at 37° C., with 88 units (0.5 µg) of uPA in PBS. Urokinase activity was measured using uPA Activity Assay Kit as described earlier.

Figure 2:
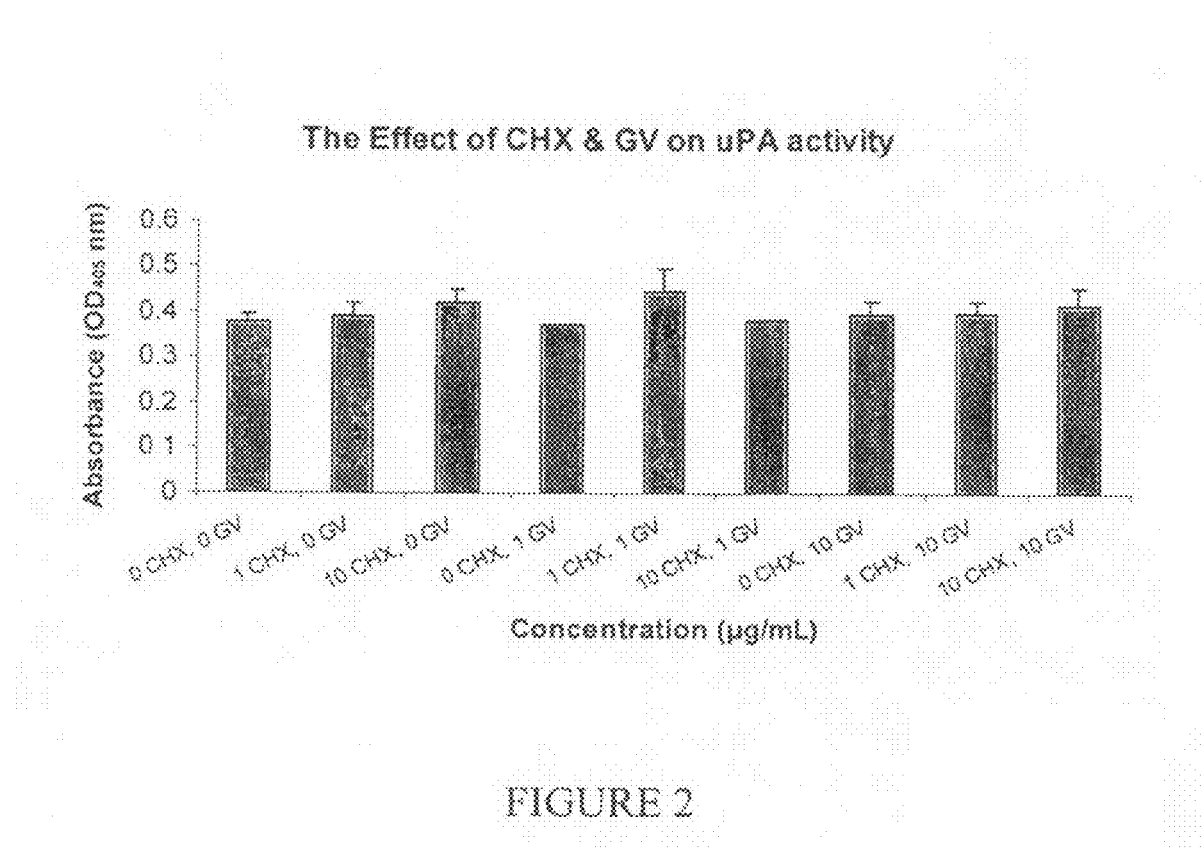
FIG. 2. Urokinase activity in the presence of chlorhexidine and gentian violet. Concentrations of chlorhexidine (CHX) and gentian violet (GV) are indicated in μg/mL.
Figure 3:
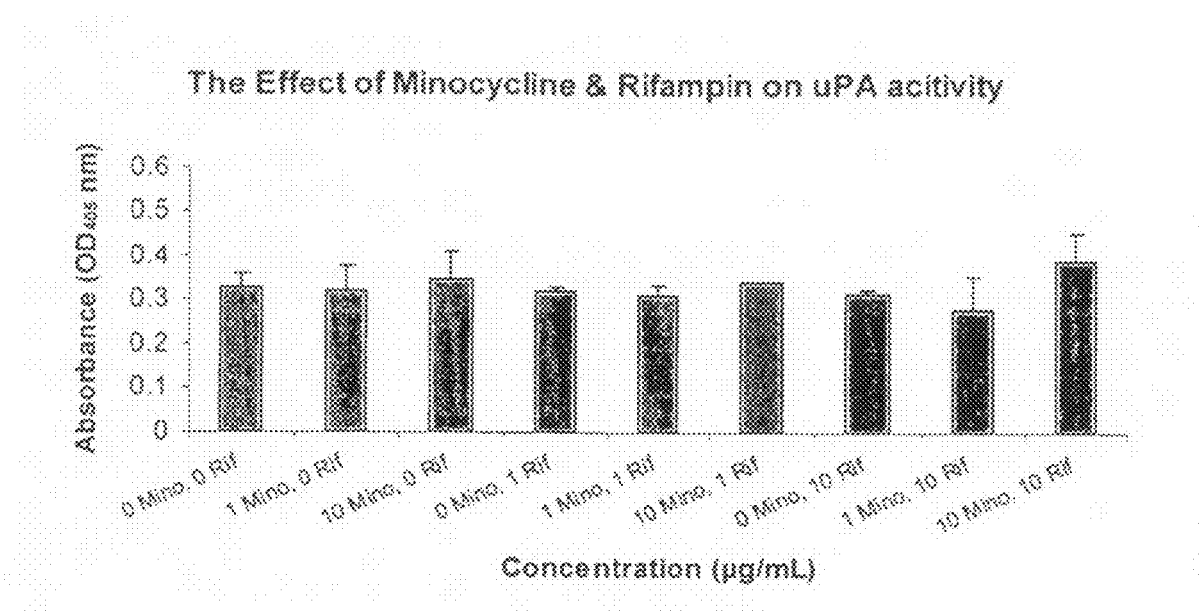
FIG. 3. Urokinase activity in the presence of minocycline and rifampin. Concentrations of minocycline (Mino) and rifampin (Rif) are indicated in μg/mL.

Urokinase activity was not adversely affected by either CHX or GV, or by their combination, or by minocycline or rifampin, or by their combination, at concentrations up to 10 µg/mL as shown in FIGS. 2 and 3.

Figure 4:
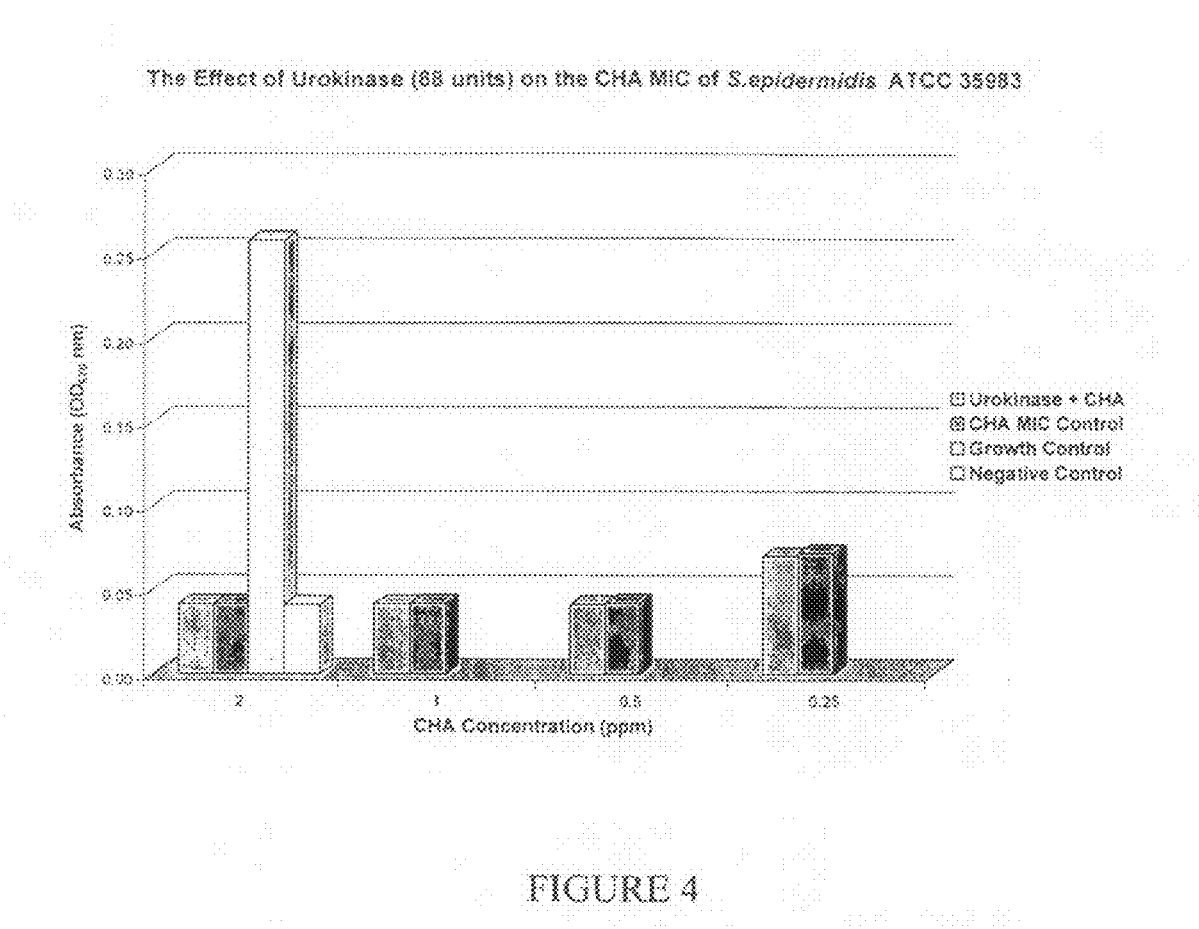
FIG. 4. Chlorhexidine activity in the presence of urokinase. Plot shows minimum inhibitory concentration (MIC) of chlorhexidine acetate (CHA) against *S. epidermidis*. CHA MIC Control=urokinase in tris-buffered saline (TBS)+CHA+Mueller-Hinton broth (MHB); Growth Control=dimethyl sulfoxide (DMSO)+TBS+*S. epidermidis*+MHB; Negative Control=DMSO+TBS+MHB.

To determine if urokinase affects the antimicrobial efficacy of chlorhexidine, the following experiment was conducted. The minimum inhibitory concentration (MIC) of chlorhexidine acetate (CHA) against *S. epidermidis* is 0.5 ppm in the absence of urokinase. Absorbance above baseline on the plot in FIG. 3 indicates growth of microbial organisms (i.e., inability to inhibit microbial growth). An increase in the MIC would be indicative of a reduction in the antimicrobial potency of CHA due to interference by Urokinase. FIG. 4 shows that the MIC of CHA was not affected by the presence of Urokinase.

Compatibility of Tissue-Type Plasminogen Activator (tPA) with Antiseptic and Antibiotic agents Different combinations of CHX, GV, minocycline and rifampin (0, 1, 10 μg/mL) were incubated overnight with 50 units of human tPA (Sigma) at 37° C., in buffer (30 mM Tris-HCl, 30 mM Imidazole, 130 mM NaCl, 1% protease free albumin). Samples were incubated with the chromogenic substrate (Sigma); tPA activity was determined by the hydrolysis of the substrate being measured continuously at 405 nm for 5 min at 50 seconds intervals. A standard curve was generated and the units plotted against the slope of the hydrolysis reaction.

Figure 5:
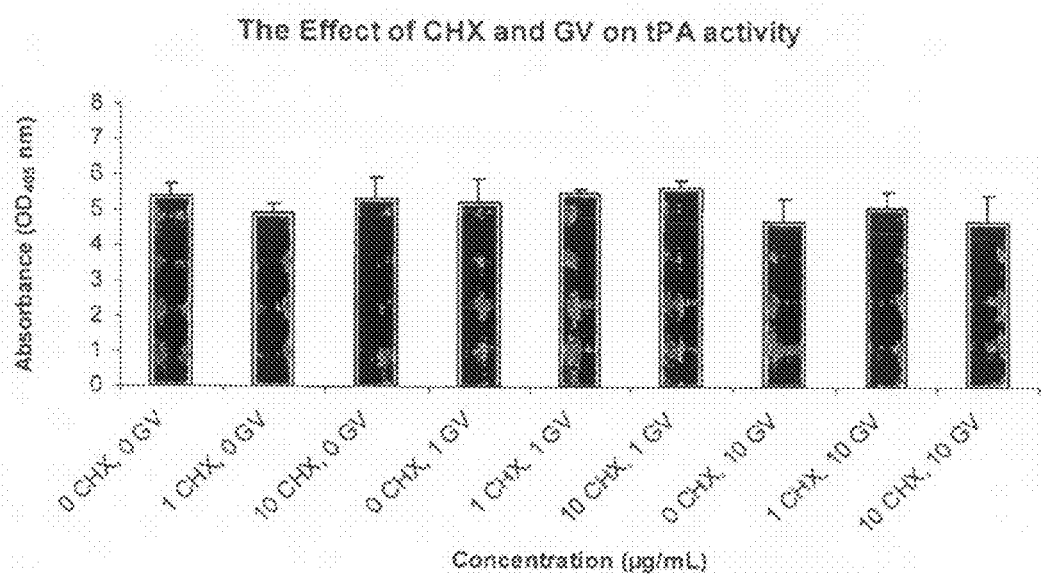
FIG. 5. Tissue-type plasminogen activator (tPA) activity in the presence of chlorhexidine and gentian violet. Concentrations of chlorhexidine (CHX) and gentian violet (GV) are indicated in μg/mL.
Figure 6:
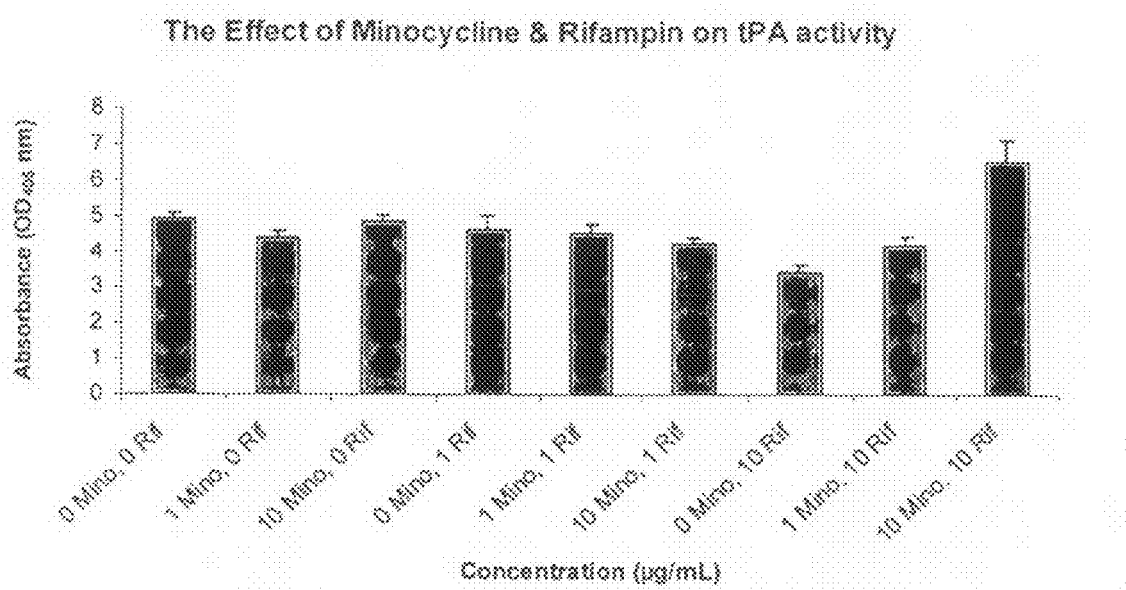
FIG. 6. Tissue-type plasminogen activator (tPA) activity in the presence of minocycline and rifampin. Concentrations of minocycline (Mino) and rifampin (Rif) are indicated in μg/mL.

As shown in FIGS. 5 and 6, tPA activity was not affected by CHX, GV, minocycline or rifampin, or by combinations thereof, at concentrations up to 10 μg/mL.

Compatibility of Streptokinase with Antiseptic and Antibiotic Agents

In a 96 well plate, different combinations of chlorhexidine (0, 1, 10 μg/mL) and gentian violet (0, 1, 10 μg/mL) were incubated overnight with 16.5 units of human streptokinase (Sigma) at 37° C., in 10 mM Tris-HCl buffer containing 0.1M NaCl and 1 mg/mL albumin. Streptokinase activity was measured using a chromogenic substrate S-2251 (Chromogenix). Samples were incubated with 0.6 mM S-2251 and 0.1 U/ml plasminogen (Sigma) for one hour. Hydrolysis of the substrate was measured at 405 nm and a standard curve was generated with the units plotted against the slope of the hydrolysis reaction.

Figure 7:
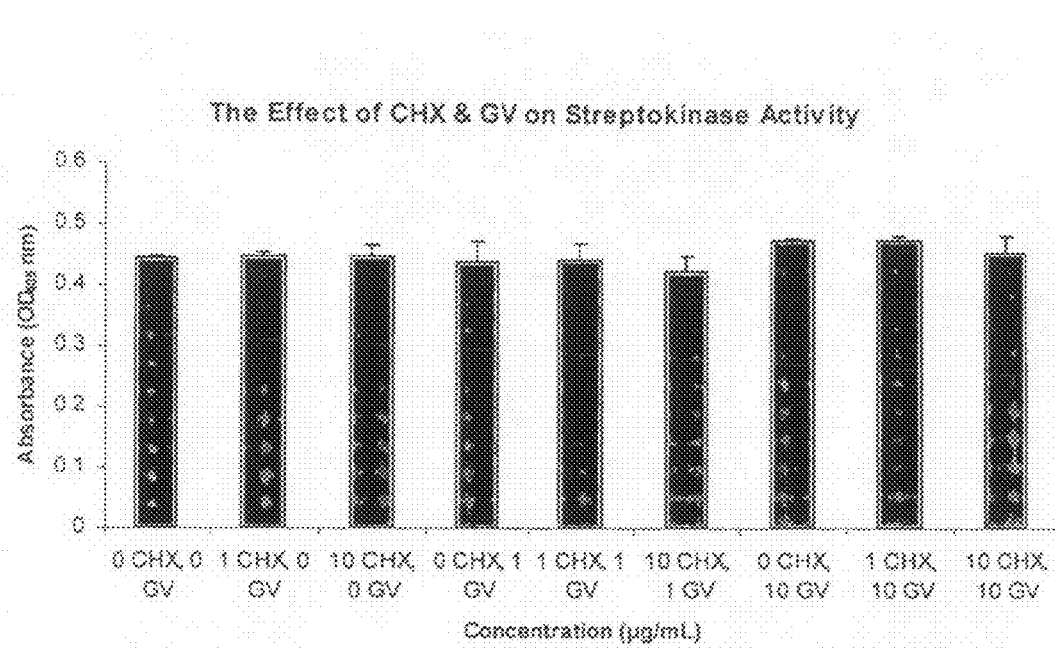
FIG. 7. Streptokinase activity in the presence of chlorhexidine and gentian violet. Concentrations of chlorhexidine (CHX) and gentian violet (GV) are indicated in μg/mL.

As shown in FIG. 7, streptokinase activity was unaffected by either CHX or GV, or by their combination, at any concentration up to 10 μg/mL.

REFERENCES

Carrasco M N, A Bueno, C D Cuevas, S Jimenez, I Salinas, A Sartorius, T Recio, M Generelo and F Ruiz-Ocaña (2004) Evaluation of a triple-lumen central venous heparin-coated catheter versus a catheter coated with chlorhexidine and silver sulfadiazine in critically ill patients. Intensive Care Med. 30: 633-638.

Hanna H, P Bahna, R Reitzel, T Dvorak, G Chaiban, R Hachem and I Raad (2006) Comparative in vitro efficacies and antimicrobial durabilities of novel antimicrobial central venous catheters. Antimicrob. Agents Chemother. 50: 3283-3288.

Harter C, H J Salwender, A Bach, G Egerer, H Goldschmidt and A D Ho (2002) Catheter-related infection and thrombosis of the internal jugular vein in hematologic-oncologic patients undergoing chemotherapy: a prospective comparison of silver-coated and uncoated catheters. Cancer 94: 245-251.

Kuter D J (2004) Thrombotic Complications of Central Venous Catheters in Cancer Patients. The Oncologist 9: 207-216.

Long D A and M G Coulthard (2006) Effect of heparin-bonded central venous catheters on the incidence of catheter-related thrombosis and infection in children and adults. Anaesth. Intensive Care 34: 481-484.

Mermel L A (2000) Prevention of intravascular catheter-related infections. Ann. Intern Med. 132: 391-402.

Pellat B, Arreto C D, Vandermander J. [Effect of chlorhexidine on bacterial fibrinolytic and collagenolytic activity] [Article in French] J. Parodontol. 1991 September; 10(3): 317-26.

Raad I I, M Luna, S A Khalil, J W Costerton, C Lam and G P Bodey (1994) The relationship between the thrombotic and infectious complications of central venous catheters. JAMA 271: 1014-1016.

Rooden C J, E F Schippers, R M Y Barge, F R Rosendaal, H F L Guiot, F J. M. van der Meer, A E Meinders, M V Huisman (2005) Infectious complications of central venous catheters increase the risk of catheter-related thrombosis in hematology patients: A prospective study. Journal of Clinical Oncology 23: 2655-2660.

Roszkowska-Jakimiec W, Jurkowski J, Ostrowska H, Worowski K. [Inhibition by ethanol and acetaldehyde the plasmin activity and plasminogen activation induced by urokinase and streptokinase] [Article in Polish]. Rocz Akad Med. Bialymst. 1988-1989; 33-34:53-66.

Safdar N, Maki D G. The pathogenesis of catheter-related bloodstream infection with noncuffed short-term central venous catheters. Intensive Care Med. 2004 January; 30(1):62-7. Epub 2003 Nov. 26.

Saint S, Veenstra D L, Lipsky B A. The clinical and economic consequences of nosocomial central venous catheter-related infection: are antimicrobial catheters useful? Infect Control Hosp Epidemiol. 2000 June; 21(6):375-80.

U.S. Pat. No. 4,273,873, issued Jun. 16, 1981. Sugitachi et al. Preparation of antithrombogenic polymeric material.

U.S. Pat. No. 4,378,435, issued Mar. 29, 1983. Takagi et al. Process of providing enzyme activity to a solid surface.

U.S. Pat. No. 4,483,922, issued Nov. 20, 1984. Carpenter et al. Inactivation of enzymes.

U.S. Pat. No. 5,451,424, issued Sep. 19, 1995, Solomon et al., Anti-infective and antithrombogenic medical articles and method for their preparation.

U.S. Pat. No. 5,688,516, issued Nov. 18, 1997. Raad et al. Non-glycopeptide antimicrobial agents in combination with an anticoagulant, an antithrombotic or a chelating agent, and their uses in, for example, the preparation of medical devices.

U.S. Pat. No. 5,707,366, issued Jan. 13, 1998, Solomon et al., Anti-infective and antithrombogenic medical articles and method for their preparation.

U.S. Pat. No. 6,261,271, issued Jul. 17, 2001, Solomon et al., Anti-infective and antithrombogenic medical articles and method for their preparation.

U.S. Pat. No. 6,273,875 B1, issued Aug. 14, 2001. Siman et al. Medical devices having improved antimicrobial/antithrombogenic properties.

U.S. Pat. No. 6,528,107 B2, issued Mar. 4, 2003. Chinn et al. Method of producing antimicrobial and antithrombogenic medical devices.

U.S. Patent Application No. 2006/0257390 A1, published Nov. 16, 2006, Semba, Catheter composition and uses thereof.

What is claimed is:

1. An implantable catheter comprising, in combination, an antimicrobial agent that comprises chlorhexidine incorporated in a coating or bulk distributed combined with urokinase incorporated in a top coating, wherein the chlorhexidine does not decrease the fibrinolytic activity of the urokinase, and wherein the ratio of chlorhexidine/urokinase is 20/1 (weight/weight).

2. The implantable catheter of claim 1, wherein at least a portion of the catheter is impregnated with the antimicrobial agent.

3. The implantable catheter of claim 1, wherein at least a portion of the catheter is coated with the antimicrobial agent.

4. The implantable catheter of claim 1, wherein the antimicrobial agent further comprises gentian violet, minocycline, rifampin, minocycline-rifampin, or a salt thereof.

5. The implantable catheter of claim 4, wherein the antimicrobial agent further comprises minocycline.

6. The implantable catheter of claim 4, wherein the antimicrobial agent further comprises rifampin.

7. The implantable catheter of claim 4, wherein the antimicrobial agent further comprises minocycline-rifampin.

8. The implantable catheter of claim 1, wherein the antimicrobial agent is present in the catheter in an amount effective to permit absorption of the antimicrobial agent from the catheter.

9. The implantable catheter of claim 1, wherein the antimicrobial agent is present in a concentration of 0.01%-20% by weight of the catheter.

10. The implantable catheter of claim 1, wherein the antimicrobial agent has a concentration of about 200 micrograms per cm length of catheter.

11. The implantable catheter of claim 1, wherein the urokinase is present in the catheter in an amount effective to permit absorption of the urokinase from the catheter.

12. The implantable catheter of claim 1, wherein the urokinase is present in the catheter from 1 U-1000 U per cm length of catheter or wherein the urokinase is present in the catheter from 10 U-500 U per cm length of catheter.

13. The implantable catheter of claim 1, wherein the catheter is a transcutaneous catheter, a catheter for implantation in a blood vessel or a body cavity, a venous catheter, an arterial catheter or a dialysis catheter.

14. The implantable catheter of claim 1, wherein the wherein the antimicrobial agent is present in a concentration of 0.1%-10% by weight of the catheter.

15. The implantable catheter of claim 1, wherein the urokinase is present in the catheter from 10 U-500 U per cm length of catheter.

16. The implantable catheter of claim 1, further comprising gentian violet, wherein the ratio of gentian violet/urokinase is 20/1.

* * * * *